United States Patent [19]

Mersch

[11] Patent Number: 5,693,049
[45] Date of Patent: Dec. 2, 1997

[54] METHOD AND APPARATUS FOR IN VIVO BLOOD IRRADIATION

[75] Inventor: Steven Henry Mersch, Germantown, Ohio

[73] Assignee: Point Source, Inc., Germantown, Ohio

[21] Appl. No.: 398,459

[22] Filed: Mar. 3, 1995

[51] Int. Cl.$^6$ .................................................. A61B 17/32
[52] U.S. Cl. ...................................... 606/15; 607/89
[58] Field of Search ...................... 606/7, 14, 15, 606/16, 17, 10, 11, 12; 607/89

[56] References Cited

U.S. PATENT DOCUMENTS

| | | |
|---|---|---|
| 5,042,980 | 8/1991 | Baker et al. |
| 5,151,096 | 9/1992 | Khoury |
| 5,169,395 | 12/1992 | Narisco, Jr. .................. 606/7 |
| 5,250,068 | 10/1993 | Ideguchi et al. |
| 5,344,419 | 9/1994 | Spears .......................... 606/15 |
| 5,415,655 | 5/1995 | Fuller et al. .................. 606/16 |
| 5,478,338 | 12/1995 | Reynard ......................... 606/17 |
| 5,527,308 | 6/1996 | Anderson et al. ............. 606/14 |
| 5,534,000 | 7/1996 | Bruce ............................. 606/17 |

*Primary Examiner*—Lee S. Cohen
*Assistant Examiner*—Sonya Harris-Ogugua
*Attorney, Agent, or Firm*—Killworth, Gottman, Hagan & Schaeff, LLP

[57] ABSTRACT

In vivo irradiation of blood is performed via catheters which can also or alternately be used to introduce fluids into blood vessels. The catheters include narrow tubular portions which are at least partially inserted into blood vessels. The narrow tubular portions utilize optical material to carry light radiation into blood vessels for irradiation of blood therein. In some embodiments, the tubular portions of the catheters are made of optical material to directly carry light radiation. The tubular portions are then made to diffuse the light along at least a portion of their lengths or to carry light to diffusing and preferably radio-opaque tips from which the majority of the light is diffused. In alternate embodiments, the tubular portions include inner catheter tubes covered with thin outer sleeves made of optical material and tapered and/or otherwise adapted to diffuse light radiation along their lengths, preferably primarily along the portions of their lengths received within blood vessels, or at their ends. Light radiation is coupled into the catheters by optical couplers formed as portions of the narrow tubular portions of the catheters, as portions of hubs which receive the narrow tubular portions of the catheters or as integral portions of catheters formed as unitary structures. The catheters include luer fittings for coupling fluid carrying tubes and light sources thereto, and preferably include tapered luer fittings for the optical couplers to facilitate connection of light sources, such as lasers, to the optical couplers.

21 Claims, 1 Drawing Sheet

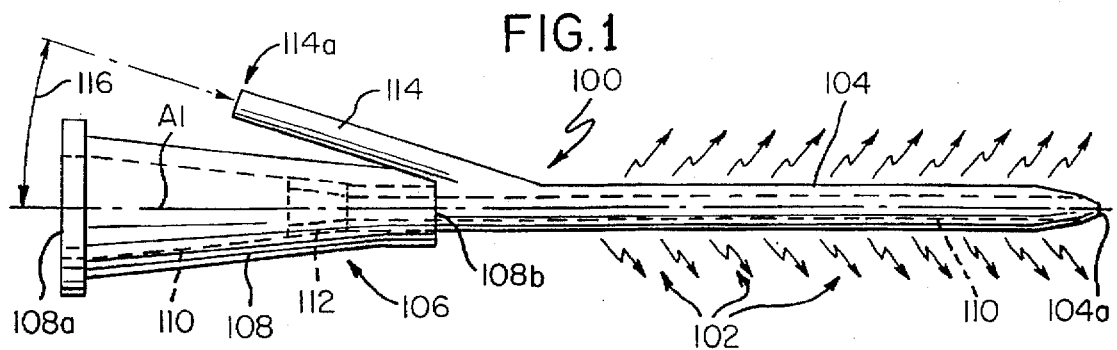
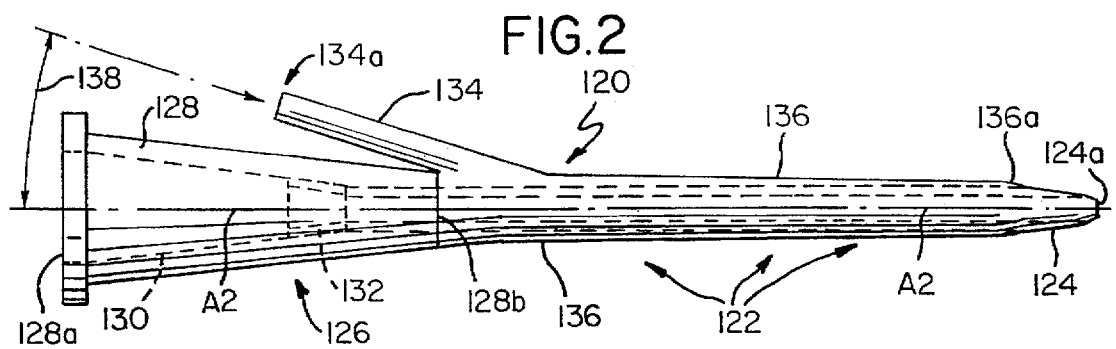
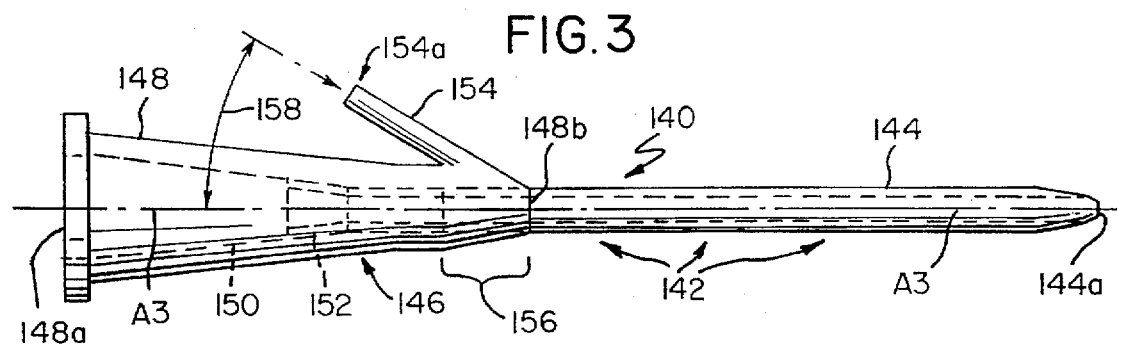
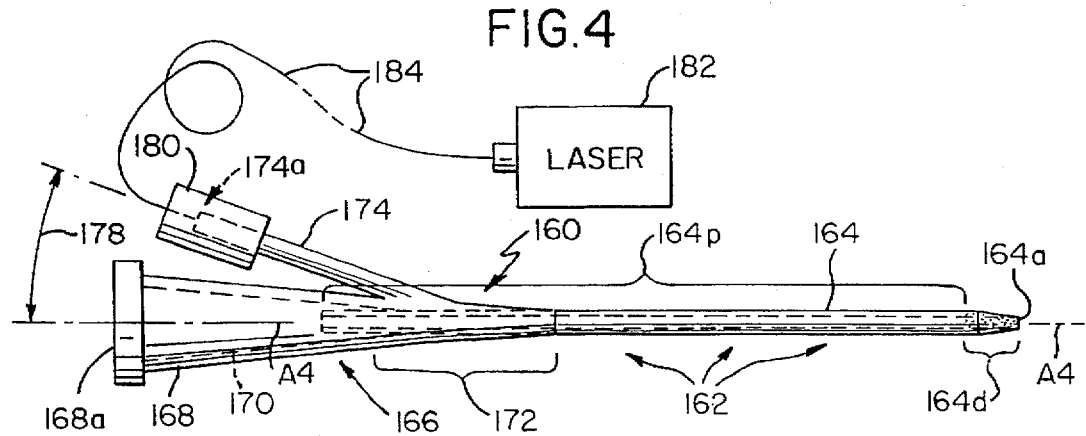

METHOD AND APPARATUS FOR IN VIVO BLOOD IRRADIATION

BACKGROUND OF THE INVENTION

The present invention relates in general to in vivo irradiation of blood and, more particularly, to a method and apparatus for irradiating blood in a blood vessel by means of a catheter which also may be used to introduce fluids into the blood vessel.

The use of light in medicine is well known dating back at least to the late 1920s when ultraviolet blood irradiation therapy developed out of an attempt to use the bactericidal properties of ultraviolet light in the treatment of blood stream infections. This treatment was developed and administered by a Dr. Knott and led to the "Knott Technic of Ultraviolet Blood Irradiation". In the 1930s and 1940s, thousands of patients were treated with the Knott Technic by numerous doctors with very positive results.

Even so, the Knott Technic was effectively abandoned due to a variety of factors. For one, the Knott technic required an invasive procedure to place an exposure chamber within a patient's circulatory system. In addition, at that time, the ultraviolet light generator was expensive and unwieldy. Foremost among the factors, however, was the emergence of antibiotics which were an easy and effective way to treat infections being attacked with ultraviolet light. Thus, with the exception of the use of ultraviolet light to treat bilirubin in newborn babies, optical irradiation therapy virtually disappeared during the '50s, '60s and '70s.

In the 1980s, lasers caused a rebirth of interest in light therapy. The rebirth went under the name of laser biostimulation and was claimed to aid healing and to stimulate other beneficial biological effects. Unfortunately, too often laser applications focused on the "magic" effects of lasers rather than the science of biophysics. As such, many reporting articles contained anecdotal results and little scientific evidence regarding the therapeutic effects of light.

Fortunately, recent studies have rediscovered the work done by Knott and his associates and have begun experimenting with laser light delivered through a fiber optic. This recent work is again showing positive results in the treatment of blood infections. The results of this work are even more promising and important in view of the problems faced by the medical profession in the form of viruses and bacteria which are becoming more and more resistant to available antibiotics. Of more concern, viruses and bacteria now appear to be resistant even to antibiotics under test for future use.

While the use of blood irradiation is promising as an alternative to antibiotics in combating blood infections and many of the problems associated with blood irradiation have been overcome, such as the development of inexpensive light sources, the invasive nature of blood irradiation remains. Thus, there is a need for an improved arrangement for administering blood irradiation to facilitate further development of this promising ally of faltering antibiotics.

SUMMARY OF THE INVENTION

This need is met by the invention of the present application wherein an improved method and apparatus provide for in vivo irradiation of blood via catheters. Catheters of the present invention can be used to introduce fluids into blood vessels of patients in a conventional manner and/or to irradiate blood within blood vessels into which the catheters are inserted. The catheters include narrow tubular portions which are at least partially inserted into blood vessels. The narrow tubular portions utilize optical material and are adapted to carry light radiation into blood vessels for irradiation of blood within the vessels.

For some embodiments of the invention, the tubular portions of the catheters themselves are made of optical material to directly carry light radiation. The tubular portions are then made to diffuse the light along their lengths or to carry light to diffusing and preferably radio-opaque tips from which the majority of the light is diffused into blood vessels. In alternate embodiments, the tubular portions include inner catheter tubes which are covered with thin outer sleeves. The thin outer sleeves are then made of optical material and tapered and/or otherwise adapted to diffuse light radiation along their lengths, preferably primarily along the portions of their lengths which are received within blood vessels, or at their ends.

Light radiation is coupled into the catheters by optical couplers which can be formed as portions of the narrow tubular portions of the catheters, as portions of hubs which receive the narrow tubular portions of the catheters or as integral portions of catheters formed as unitary structures. The catheters include luer fittings for coupling fluid carrying tubes and light sources thereto, and preferably include tapered luer fittings for the optical couplers to facilitate connection of light sources, such as lasers, to the optical couplers.

In accordance with one aspect of the present invention, apparatus for in vivo irradiation of blood comprises a tubular catheter having a proximal end, a distal end and a central axis with the distal end of the tubular catheter being adapted to be received within a blood vessel. An optical coupler couples light radiation to the tubular catheter which diffuses received light radiation outwardly therefrom into the blood vessel.

The tubular catheter may comprise an inner catheter tube covered by an outer sleeve formed of optical material. For this embodiment, the optical coupler couples light radiation to the outer sleeve and the optical coupler may comprise an extension of the outer sleeve. To enhance the optical interface between the optical coupler and the tubular catheter, the optical coupler preferably extends toward the proximal end of the catheter at an acute angle relative to the central axis of the catheter. To substantially evenly diffuse light from the tubular catheter along at least a portion of its length, that portion of the outer sleeve may be tapered in thickness from the proximal end of the tubular catheter to the distal end of the tubular catheter.

Alternately, the tubular catheter may be formed of optical material which is optically diffusing along at least a portion of its length, preferably the portion which extends into a blood vessel. For this embodiment, the optical coupler may comprise an extension of the tubular catheter. Here again, to enhance the optical interface between the optical coupler and the tubular catheter, the optical coupler preferably extends toward the proximal end of the catheter at an acute angle relative to the central axis of the catheter. It may be preferred in some instances to form the proximal end of the tubular catheter of optically clear material and the distal end of the catheter of optically diffusing material such that a substantial portion of the irradiation occurs at the tip end of the catheter.

In accordance with another aspect of the present invention, apparatus for in vivo irradiation of blood comprises a tubular catheter assembly having a proximal end for receiving intravenous fluids, a distal end adapted to be received within a blood vessel for discharging the intravenous fluids therein and a central axis. The tubular catheter assembly includes an optical coupler for receiving light radiation which is transmitted to and diffused outwardly through the distal end of the tubular catheter assembly into the blood vessel. The tubular catheter assembly may comprise an inner catheter tube with an outer sleeve formed of optical material covering the inner catheter tube. For this embodiment, the optical coupler couples light radiation to the outer sleeve and may form an extension of the outer sleeve.

Alternately, the tubular catheter assembly may comprise a tubular catheter formed of optical material which is optically diffusing along at least a portion of its length and the optical coupler may comprise an extension of the tubular catheter. It may be preferred in some instances to form the proximal end of the catheter assembly of optically clear material and the distal end of the catheter assembly of optically diffusing material such that a substantial portion of the irradiation occurs at the tip end of the catheter assembly.

In some embodiments, the tubular catheter assembly may comprise a catheter tube and a hub attached thereto. For these embodiments, the catheter tube defines the distal end of the tubular catheter assembly and the hub defines the proximal end of the tubular catheter assembly and may also define the optical coupler.

In accordance with yet another aspect of the present invention, a method for in vivo irradiation of blood comprises the steps of: inserting a catheter into a blood vessel for carrying intravenous fluids into the blood vessel; coupling light radiation into the catheter; and, diffusing received light radiation outwardly from the catheter into the blood vessel.

The step of diffusing received light radiation outwardly from the catheter into the blood vessel may comprise the step of diffusing received light radiation along a substantial length of the catheter which is inserted into the blood vessel. Alternately, the step of diffusing received light radiation outwardly from the catheter into the blood vessel may comprise the step of diffusing received light radiation from the distal end of the catheter.

The step of coupling light radiation into the catheter may comprise the steps of: coupling light radiation into a hub of the catheter; and, optically coupling the hub to a catheter tube of the catheter, the hub and catheter tube being made of optical material. Alternately, the step of coupling light radiation into the catheter may comprise coupling light radiation into an outer sleeve formed of optical material and covering an inner catheter tube of the catheter. The method may further comprise the step of tapering the sleeve along at least a portion of its length to diffuse light radiation along a corresponding portion of the catheter.

It is thus an object of the present invention to provide an improved method and apparatus for in vivo irradiation of blood via catheters inserted into blood vessels; to provide an improved method and apparatus for in vivo irradiation of blood via catheters formed of optical material or covered by outer sleeves formed of optical material; and, to provide an improved method and apparatus for in vivo irradiation of blood via catheters wherein light radiation is coupled to the catheters via optical couplers associated with portions of the catheters received within blood vessels and provided on those portions or on hubs connected or formed to those portions.

Other objects and advantages of the invention will be apparent from the following description, the accompanying drawings and the appended claims.

BRIEF DESCRIPTION OF THE DRAWINGS

FIG. 1 is a schematic side view of a first embodiment of catheter apparatus of the present invention;

FIG. 2 is a schematic side view of a second embodiment of catheter apparatus of the present invention;

FIG. 3 is a schematic side view of a third embodiment of catheter apparatus of the present invention; and FIG. 4 is a schematic view of apparatus operable in accordance with the present invention for the in vivo irradiation of blood including a fourth embodiment of catheter apparatus of the present invention.

DETAILED DESCRIPTION OF THE INVENTION

Reference will now be made to the drawing figures wherein FIG. 1 illustrates a first embodiment of catheter apparatus 100 operable in accordance with the present invention. The catheter apparatus 100 comprises a tubular catheter having a distal end 102 defined by a catheter tube 104, a proximal end 106 defined by a hub 108 and a central axis A1. The distal end 102 of the catheter apparatus 100 is adapted to be received within a blood vessel in a manner conventional with catheters for passing fluids to a blood vessel. Fluids pass through the catheter apparatus 100 via a passageway 110 extending from the base 108a of the hub 108 to the tip 104a of the catheter tube 104. The hub 108 typically defines a luer fitting for receiving a mating luer fitting of a tube carrying fluids to be introduced into a blood vessel. In the first embodiment of FIG. 1, the catheter tube 104 is secured to the hub 108 in a conventional manner by a ferrule 112 which is swaged into the area joining the catheter tube 104 and the hub 108.

An optical coupler 114 couples light radiation to the distal end 102 of the tubular catheter where received light radiation is diffused outwardly into a blood vessel receiving the tubular catheter to thereby irradiate blood flowing through the blood vessel. In the first embodiment of FIG. 1, the distal end 102 of the tubular catheter is formed of optical material which is optically diffusing.

"Optical material" is used herein to refer to material which is intended to conduct light energy. Optical material which is "optically clear" is used herein to refer to material used for conveying light energy which material is substantially clear at desired light wavelengths and which has an index of refraction greater than the index of refraction of typical body fluids ($\approx 1.35$). For such optical material, light can propagate in the material via substantially total internal reflection (TIR) when the material is placed in body fluids such as blood. Optical material which is "optically diffusing" is used herein to refer to material used for conveying light energy but which material has diffusing particles or materials dispersed therein or is otherwise treated to defeat TIR propagation of light within the material such that light is emitted from the material.

Accordingly, in the first embodiment of FIG. 1, light radiation coupled to the tubular catheter is diffused along substantially the entire length of the distal end 102 of the tubular catheter which extends from the tip 108b of the hub 108 to the tip 104a of the catheter tube 104. It may be desired to make the portion of the catheter tube 104 of the tubular catheter adjacent to the tip 108b of the hub 108 optically clear to prevent substantial diffusion of light radiation therefrom since this portion of the catheter tube 104 would typically not be inserted into a blood vessel.

The optical coupler 114 in the first embodiment of FIG. 1 comprises an extension of the catheter tube 104. The optical coupler 114 is oriented at an acute angle 116 relative to the central axis A1 of the catheter apparatus 100 to better couple light radiation into the catheter tube 104. Preferably the tip 114a of the optical coupler 114 defines a tapered luer fitting to facilitate connection of a light source to the optical coupler 114.

A second embodiment of catheter apparatus 120 operable in accordance with the present invention is illustrated in FIG. 2. The catheter apparatus 120 comprises a tubular catheter having a distal end 122 defined by an inner catheter tube 124, a proximal end 126 defined by a hub 128 and a central axis A2. The distal end 122 of the catheter apparatus 120 is adapted to be received within a blood vessel in a manner conventional with catheters for passing fluids to a blood vessel. Fluids pass through the catheter apparatus 120 via a passageway 130 extending from the base 128a of the hub 128 to the tip 124a of the inner catheter tube 124. The hub 128 typically defines a luer fitting for receiving a mating luer fitting of a tube carrying fluids to be introduced into a blood vessel. In the second embodiment of FIG. 2, the inner catheter tube 124 is secured to the hub 128 in a conventional manner by a ferrule 132 which is swaged into the area joining the inner catheter tube 124 and the hub 128.

An optical coupler 134 couples light radiation to the distal end 122 of the tubular catheter where received light radiation is diffused outwardly into a blood vessel receiving the tubular catheter to thereby irradiate blood flowing through the blood vessel. In the second embodiment of FIG. 2, the optical coupler 134 couples light radiation to an outer sleeve 136 formed of an optical material and covering the inner catheter tube 124. In the illustrated second embodiment of FIG. 2, the outer sleeve 136 is tapered in thickness from the tip 128b of the hub 128 of the tubular catheter to the distal end 122 of the tubular catheter such that light radiation coupled to the tubular catheter is diffused along substantially the entire length of the distal end 122 of the tubular catheter, i.e., from the tip 128b of the hub 128 to the end 136a of the outer sleeve 136. It may be desired to make the portion of the outer sleeve 136 adjacent to the tip 128b of the hub 128 with little or no taper to prevent substantial diffusion of light radiation therefrom since this portion of the distal end 122 of the tubular catheter would typically not be inserted into a blood vessel.

The optical coupler 134 in the second embodiment of FIG. 2 comprises an extension of the outer sleeve 136. The optical coupler 134 is oriented at an acute angle 138 relative to the central axis A2 of the catheter apparatus 120 to better couple light radiation into the outer sleeve 136. Preferably the tip 134a of the optical coupler 134 defines a tapered luer fitting to facilitate connection of a light source to the optical coupler 134.

A third embodiment of catheter apparatus 140 operable in accordance with the present invention is illustrated in FIG. 3. The catheter apparatus 140 comprises a tubular catheter having a distal end 142 defined by a catheter tube 144, a proximal end 146 defined by a hub 148 and a central axis A3. The distal end 142 of the catheter apparatus 140 is adapted to be received within a blood vessel in a manner conventional with catheters for passing fluids to a blood vessel. Fluids pass through the catheter apparatus 140 via a passageway 150 extending from the base 148a of the hub 148 to the tip 144a of the catheter tube 144. The hub 148 typically defines a luer fitting for receiving a mating luer fitting of a tube carrying fluids to be introduced into a blood vessel.

In the third embodiment of FIG. 3, the catheter tube 144 is secured to the hub 148 in a conventional manner by a ferrule 152 which is swaged into the area joining the catheter tube 144 and the hub 148. The catheter tube 144 is formed of optical material which is optically diffusing over at least a substantial portion of its length from the tip 148b of the hub 148 to the tip 144a of the catheter tube 144. The portion of the catheter tube 144 which is optically diffusing should correspond approximately to the portion which is normally inserted into a blood vessel for use of the catheter apparatus 140. To this end, it may be desired to make a portion of the catheter tube 144 of the tubular catheter adjacent to the tip 148b of the hub 148 optically clear to prevent substantial diffusion of light radiation therefrom since this portion of the catheter tube 144 would typically not be inserted into a blood vessel.

An optical coupler 154 couples light radiation to the distal end 142 of the tubular catheter where received light radiation is diffused outwardly into a blood vessel receiving the tubular catheter to thereby irradiate blood flowing through the blood vessel. In the third embodiment of FIG. 3, the optical coupler 154 is formed as a part of the hub 148 and the catheter tube 144 is coupled to the hub 148 to provide optical continuity for the light to efficiently pass from the hub 148 to the catheter tube 144. The ferrule 152 which is swaged into the area joining the catheter tube 144 and the hub 148 does not ensure optical continuity. Accordingly, to index match the catheter tube 144 to the hub 148, an optical epoxy is used over at least a portion 156 of the coupling area. It is also possible to insert mold the catheter tube 144 to the hub 148 or to form the catheter tube 144 and the hub 148 as an integral part.

The optical coupler 154 is oriented at an acute angle 158 relative to the central axis A3 of the catheter apparatus 140 to better couple light radiation into the hub 148 and from there into the catheter tube 144. Preferably the tip 154a of the optical coupler 154 defines a tapered luer fitting to facilitate connection of a light source to the optical coupler 154.

A fourth embodiment of catheter apparatus 160 operable in accordance with the present invention is illustrated in the apparatus of FIG. 4. The catheter apparatus 160 comprises a tubular catheter having a distal end 162 defined by a catheter tube 164, a proximal end 166 defined by a hub 168 and a central axis A4. The distal end 162 of the catheter apparatus 160 is adapted to be received within a blood vessel in a manner conventional with catheters for passing fluids to a blood vessel. Fluids pass through the catheter apparatus 140 via a passageway 170 extending from the base 168a of the hub 168 to the tip 164a of the catheter tube 164. The hub 168 typically defines a luer fitting for receiving a mating luer fitting of a tube carrying fluids to be introduced into a blood vessel.

In the fourth embodiment of FIG. 4, the catheter tube 164 is secured to the hub 168 by an optical epoxy which is used over at least a portion 172 of the coupling area. It is also possible to insert mold the catheter tube 164 to the hub 168 or to form the catheter tube 164 and the hub 168 as an integral part. The proximal end 164p of the catheter tube 164 is formed of optical material which can be optically diffusing but is preferably and as illustrated optically clear. The distal tip 164d of the catheter tube 164 is formed of optical material which is optically diffusing and is also preferably radio-opaque. The distal tip 164d is thermally welded to the catheter tube 164 using well know technology and is tapered as illustrated to form the tip of the catheter. An optical coupler 174 couples light radiation to the catheter tube 164.

Once light radiation is introduced into the catheter tube 164 via the optical coupler 174, the light travels within the hub 168 and down the proximal end 164p of the catheter tube 164 via total internal reflection (TIR) toward the distal tip 164d of the catheter tube 164. At the distal tip 164d, the combination of diffusing particles and the tapering wall cause the light radiation to leave the catheter tube 164 and irradiate blood within a blood vessel to produce a desired therapeutic effect.

In the fourth embodiment of FIG. 4, the optical coupler 174 is formed as a part of the hub 168 as in the third embodiment of FIG. 3 and is oriented at an acute angle 178 relative to the central axis A4 of the catheter apparatus 160 to better couple light radiation into the hub 168 and from there into the catheter tube 164. Preferably the tip 174a of the optical coupler 174 defines a male tapered luer fitting to facilitate connection of a light source to the optical coupler 154.

In the apparatus illustrated in FIG. 4, the male tapered luer fitting defined by the tip 174a is received by a female tapered luer fitting 180 which is connected to a light source, illustrated as a laser 182, by means of an optical fiber 184. While higher power levels may ultimately be used, it is currently believed that desired therapeutic effects will be achieved with low-energy levels such that the maximum average optical power level required for operation of the catheter apparatus is anticipated not to exceed 20 milliwatts (mw).

Further, it is currently contemplated that light ranging in wavelength from approximately 0.3 micron to approximately 1.0 micron will be used in the present invention. However, it should be apparent that any wavelength of light found to have therapeutic properties when used to irradiate blood can be used.

Having thus described the invention of the present application in detail and by reference to preferred embodiments thereof, it will be apparent that modifications and variations are possible without departing from the scope of the invention defined in the appended claims.

What is claimed is:

1. Apparatus for in vivo irradiation of blood comprising:
    a tubular catheter having a proximal end, a distal end and a central axis, said distal end adapted to be received within a blood vessel so that blood flowing through the blood vessel flows over said distal end of said tubular catheter within said blood vessel; and
    an optical coupler associated with said proximal end of said tubular catheter for coupling light radiation to said tubular catheter which diffuses received light radiation outwardly therefrom within said blood vessel to irradiate blood flowing through said blood vessel.

2. Apparatus for in vivo irradiation of blood as claimed in claim 1 wherein said tubular catheter comprises:
    an inner catheter tube; and
    an outer sleeve formed of optical material and covering said inner catheter tube, said optical coupler coupling light radiation to said outer sleeve.

3. Apparatus for in vivo irradiation of blood as claimed in claim 2 wherein said outer sleeve is tapered in thickness along at least a portion thereof from said proximal end of said tubular catheter to said distal end of said tubular catheter.

4. Apparatus for in vivo irradiation of blood as claimed in claim 2 wherein said optical coupler comprises an extension of said outer sleeve.

5. Apparatus for in vivo irradiation of blood as claimed in claim 4 wherein said extension of said outer sleeve extends toward the proximal end of said tubular catheter at an acute angle relative to said central axis of said tubular catheter.

6. Apparatus for in vivo irradiation of blood as claimed in claim 1 wherein said tubular catheter is formed of optical material which is optically diffusing along at least a portion of a length of said tubular catheter.

7. Apparatus for in vivo irradiation of blood as claimed in claim 6 wherein said optical coupler comprises an extension of said tubular catheter.

8. Apparatus for in vivo irradiation of blood as claimed in claim 7 wherein said extension of said tubular catheter extends toward the proximal end of said tubular catheter at an acute angle relative to central axis of said tubular catheter.

9. Apparatus for in vivo irradiation of blood as claimed in claim 1 wherein the proximal end of said tubular catheter is formed of optical material which is optically clear and the distal end of said catheter is formed of optical material which is optically diffusing.

10. Apparatus for in vivo irradiation of blood comprising a tubular catheter assembly having a central axis, a proximal end for receiving intravenous fluids and a distal end adapted to be received within a blood vessel so that blood flowing through the blood vessel flows over said distal end of said tubular catheter within aid blood vessel and said intravenous fluids can be discharged into said blood vessel through said tubular catheter assembly, said tubular catheter assembly including an optical coupler associated with said proximal end of said tubular catheter assembly for receiving light radiation which is transmitted to and diffused outwardly through said distal end of said tubular catheter assembly within said blood vessel to irradiate blood flowing through said blood vessel.

11. Apparatus for in vivo irradiation of blood as claimed in claim 10 wherein said tubular catheter assembly comprises:
    an inner catheter tube; and
    an outer sleeve formed of optical material and covering said inner catheter tube, said optical coupler coupling light radiation to said outer sleeve.

12. Apparatus for in vivo irradiation of blood as claimed in claim 11 wherein said optical coupler comprises an extension of said outer sleeve.

13. Apparatus for in vivo irradiation of blood as claimed in claim 10 wherein said tubular catheter assembly comprises a tubular catheter formed of optical material which is optically diffusing along at least a portion of its length and said optical coupler comprises an extension of said tubular catheter.

14. Apparatus for in vivo irradiation of blood as claimed in claim 10 wherein said distal end of said catheter assembly is formed of optically clear material and the tip of said distal end of said catheter assembly is formed of optically diffusing material.

15. Apparatus for in vivo irradiation of blood as claimed in claim 10 wherein said tubular catheter assembly comprises a catheter tube and a hub attached thereto, said catheter tube defining said distal end of said tubular catheter assembly and said hub defining said proximal end of said tubular catheter assembly and said optical coupler.

16. A method for in vivo irradiation of blood comprising the steps of:
    inserting a tubular catheter into a blood vessel for carrying intravenous fluids into said blood vessel with said tubular catheter being received within said blood vessel so that blood flowing through said blood vessel flows over said tubular catheter within said blood vessel;
    coupling light radiation into said tubular catheter; and
    diffusing received light radiation outwardly from said tubular catheter within said blood vessel to irradiate blood flowing through said blood vessel.

17. The method of in vivo irradiation of blood as claimed in claim 16 wherein said step of diffusing received light radiation outwardly from said tubular catheter into said blood vessel comprises the step of diffusing received light radiation along a substantial length of said tubular catheter which is inserted into said blood vessel.

18. The method of in vivo irradiation of blood as claimed in claim 16 wherein said step of diffusing received light radiation outwardly from said tubular catheter into said blood vessel comprises the step of diffusing received light radiation from the distal end of said tubular catheter.

19. The method of in vivo irradiation of blood as claimed in claim 16 wherein said step of coupling light radiation into said tubular catheter comprises the steps of:

coupling light radiation into a hub of said tubular catheter; and optically coupling said hub to a catheter tube of said tubular catheter, said hub and said catheter tube being made of optical material.

20. The method of in vivo irradiation of blood as claimed in claim 16 wherein said step of coupling light radiation into said tubular catheter comprises coupling light radiation into an outer sleeve formed of optical material and covering an inner catheter tube of said tubular catheter.

21. The method of in vivo irradiation of blood as claimed in claim 20 wherein said step of diffusing received light radiation outwardly from said tubular catheter comprises the step of diffusing received radiation along at least a portion of said sleeve length which is tapered to diffuse light radiation along said tapered portion of said tubular catheter.

* * * * *

UNITED STATES PATENT AND TRADEMARK OFFICE
CERTIFICATE OF CORRECTION

PATENT NO. : 5,693,049
DATED : December 2, 1997
INVENTOR(S) : Steven Henry Mersch It is certified that error appears in the above-indentified patent and that said Letters Patent is hereby corrected as shown below:

Delete Claim 1 and insert in its place:

--1. Apparatus for in vivo irradiation of blood comprising:
 a tubular catheter having an outer surface, a proximal end, a distal end and a central axis, said tubular catheter formed at least in part of optical material, said distal end adapted to be received within a blood vessel so that blood flowing through the blood vessel flows over said distal end of said tubular catheter within said blood vessel and is in contact with said outer surface of said tubular catheter, said proximal end of said tubular catheter remaining outside said blood vessel; and
 an optical coupler located adjacent said proximal end of said tubular catheter for coupling light radiation to said tubular catheter, at least a portion of said tubular catheter adjacent said outer surface of said distal end of said tubular catheter being optically diffusing to diffuse received light radiation outwardly therefrom within said blood vessel to irradiate blood flowing through said blood vessel, said light radiation being transmitted internally within said optical material of said tubular catheter.--

Delete Claim 2 and insert in its place:

--2. Apparatus for in vivo irradiation of blood as claimed in claim 1 wherein said tubular catheter comprises:
 an inner catheter tube; and
 an outer sleeve formed of said optical material and covering said inner catheter tube, said optical coupler coupling light radiation to said outer sleeve for transmission internally within said outer sleeve.--

Col. 8, line 11, "to central axis" should be --to said central axis--.

UNITED STATES PATENT AND TRADEMARK OFFICE
CERTIFICATE OF CORRECTION

PATENT NO. : 5,693,049
DATED : December 2, 1997
INVENTOR(S) : Steven Henry Mersch It is certified that error appears in the above-indentified patent and that said Letters Patent is hereby corrected as shown below:

Delete Claim 10 and insert in its place:

--10. Apparatus for in vivo irradiation of blood comprising a tubular catheter assembly formed at least in part of optical material and having an outer surface, a central axis, a proximal end for receiving intravenous fluids and a distal end adapted to be received within a blood vessel so that blood flowing through the blood vessel flows over said distal end of said tubular catheter within said blood vessel and in contact with said outer surface of said tubular catheter, said proximal end of said tubular catheter remaining outside said blood vessel and said intravenous fluids can be discharged into said blood vessel through said tubular catheter assembly, said tubular catheter assembly including an optical coupler located adjacent said proximal end of said tubular catheter assembly for receiving light radiation and coupling said light radiation to said optical material of said tubular catherter assembly which light radiation is transmitted to said distal end of said tubular catheter, at least a portion of which is optically diffusing, and diffused outwardly through said distal end of said tubular catheter assembly within said blood vessel to irradiate blood flowing through said blood vessel, said light radition being transmitted internally within said optical material of said tubular catheter assembly.--

UNITED STATES PATENT AND TRADEMARK OFFICE
CERTIFICATE OF CORRECTION

PATENT NO. : 5,693,049
DATED : December 2, 1997
INVENTOR(S) : Steven Henry Mersch It is certified that error appears in the above-indentified patent and that said Letters Patent is hereby corrected as shown below:

Delete Claim 11 and insert in its place:

--11. Apparatus for in vivo irradiation of blood as claimed in claim 10 wherein said tubular catheter assembly comprises:
    an inner catheter tube; and
    an outer sleeve formed of said optical material and covering said inner catheter tube, said optical coupler coupling light radiation to said outer sleeve for transmission internally within said outer sleeve.--

Signed and Sealed this

Twenty-first Day of July, 1998

Attest:

BRUCE LEHMAN

*Attesting Officer*       *Commissioner of Patents and Trademarks*